(12) United States Patent
Vadlamani et al.

(10) Patent No.: US 11,572,386 B2
(45) Date of Patent: Feb. 7, 2023

(54) PROCESS FOR THE PREPARATION OF LINACLOTIDE

(71) Applicants: AURO PEPTIDES LTD, Hyderabad (IN); Suresh Kumar Vadlamani, Hyderabad (IN); Patil Nilesh Dagadu, Hyderabad (IN); Shafee Mohammed Abdul, Hyderabad (IN); Sanjay Devidas Patil, Hyderabad (IN); Govindrajan Narayanan, Hyderabad (IN)

(72) Inventors: Suresh Kumar Vadlamani, Hyderabad (IN); Patil Nilesh Dagadu, Hyderabad (IN); Shafee Mohammed Abdul, Hyderabad (IN); Sanjay Devidas Patil, Hyderabad (IN); Govindrajan Narayanan, Hyderabad (IN)

(73) Assignee: Auro Peptides Ltd., Hyderabad (IN)

( * ) Notice: Subject to any disclaimer, the term of this patent is extended or adjusted under 35 U.S.C. 154(b) by 1447 days.

(21) Appl. No.: 15/508,928

(22) PCT Filed: Aug. 29, 2015

(86) PCT No.: PCT/IB2015/056555
§ 371 (c)(1),
(2) Date: Mar. 5, 2017

(87) PCT Pub. No.: WO2016/038497
PCT Pub. Date: Mar. 17, 2016

(65) Prior Publication Data
US 2017/0240599 A1   Aug. 24, 2017

(30) Foreign Application Priority Data
Sep. 8, 2014 (IN) ............... 4381/CHE/2014

(51) Int. Cl.
*C07K 7/08* (2006.01)
*B01D 15/32* (2006.01)
*B01D 15/42* (2006.01)

(52) U.S. Cl.
CPC ............ *C07K 7/08* (2013.01); *B01D 15/325* (2013.01); *B01D 15/426* (2013.01)

(58) Field of Classification Search
CPC ....... C07K 7/08; B01D 15/325; B01D 15/426
See application file for complete search history.

(56) References Cited

U.S. PATENT DOCUMENTS

| | | | | |
|---|---|---|---|---|
| 2013/0190239 A1* | 7/2013 | Fretzen | ............... | A61K 9/4866 514/13.2 |
| 2014/0018307 A1* | 1/2014 | Sanghvi | ................. | A61K 47/22 514/21.1 |
| 2014/0155575 A1* | 6/2014 | Bai | ......................... | C07K 7/64 530/321 |

FOREIGN PATENT DOCUMENTS

WO   WO 2012/118972   *   9/2012   ............. C07K 14/47

OTHER PUBLICATIONS

Gongora-Benitez et al., 2013, Handles for Fmoc Solid-Phase Synthesis of Protected Peptides, ACS Comb Sci, 15: 217-228.*
Josie et al., 2010, Reversed-Phase High Performance Liquid Chromatography of Proteins, Current Protocols in Protein Science, 8.7.1-8.7.22.*
Gongora-Benitez et al., 2011, Optimized Fmoc Solid-Phase Synthesis of the Cystein-Rich Peptide Linaclotide, Biopolymers (Pept Sci), 96: 69-80.*
Tam et al., 1991, Disulfide Bond Formation in Peptides by Dimethyl Sulfoxide. Scope and Applications, J Am Chem Soc, 113: 6657-6662.*

* cited by examiner

*Primary Examiner* — Amber D Steele
(74) *Attorney, Agent, or Firm* — Jay R Akhave; PatentScience LLC

(57) ABSTRACT

The present invention relates to a process for the preparation of Linaclotide by oxidizing linear Linaclotide of formula (II) using combination of air and oxidizing agent followed by purification using RP-HPLC.

5 Claims, No Drawings
Specification includes a Sequence Listing.

```
SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Linaclotide

<400> SEQUENCE: 1

Cys Cys Glu Tyr Cys Cys Asn Pro Ala Cys Thr Gly Cys Tyr
1               5                   10
```

PROCESS FOR THE PREPARATION OF LINACLOTIDE

FIELD OF THE INVENTION

The present invention relates to a process for the preparation of Linaclotide. More particularly the present invention provides a robust process for the preparation of Linaclotide of formula (I) having high purity.

Formula (I) SEQ ID NO: 1

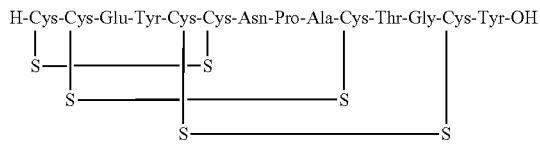

BACKGROUND OF THE INVENTION

Linaclotide is a guanylate cyclase-C (GC-C) agonist. Guanylate cyclase-C refers to a transmembrane form of guanylate cyclase that acts as the intestinal receptor for the heat-stable toxin (ST) peptides secreted by enteric bacteria. Guanylate cyclase-C is also the receptor for the naturally occurring peptides guanylin and uroguanylin.

Both Linaclotide and its active metabolite bind to GC-C and act locally on the luminal surface of the intestinal epithelium. Activation of GC-C results in an increase in both intracellular and extracellular concentrations of cyclic guanosine monophosphate (cGMP). Elevation in intracellular cGMP stimulates secretion of chloride and bicarbonate into the intestinal lumen, mainly through activation of the cystic fibrosis transmembrane conductance regulator (CFTR) ion channel, resulting in increased intestinal fluid and accelerated transit. In animal models, Linaclotide has been shown to both accelerate GI transit and reduce intestinal pain. The Linaclotide-induced reduction in visceral pain in animals is thought to be mediated by increased extracellular cGMP, which was shown to decrease the activity of pain-sensing nerves.

Linaclotide having SEQ ID NO: 1 is a peptide having 14 amino acids, with the sequence Cys Cys Glu Tyr Cys Cys Asn Pro Ala Cys Thr Gly Cys Tyr. This molecule is cyclical by forming three disulfide bonds between $Cys_1$ and $Cys_6$, between $Cys_2$ and $Cys_{10}$ and between $Cys_5$ and $Cys_{13}$.

SEQ ID NO: 1

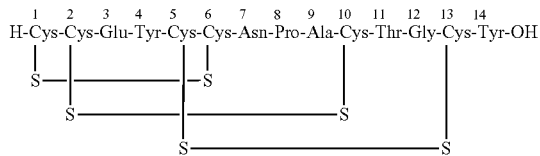

Linaclotide is marketed in USA under the trade name LINZESS in the form of capsules having dosage forms 145 mcg and 290 mcg for the treatment of irritable bowel syndrome with constipation and chronic idiopathic constipation.

Linaclotide for first time disclosed in U.S. Pat. No. 7,304,036. This patent discloses two different methods for the preparation of Linaclotide either by chemical synthesis or by recombinant DNA technology. Chemical synthesis is carried out by solid-phase method using an automated peptide synthesizer such as Cyc(4-$CH_2$Bxl)-$OCH_2$-4-(oxymethyl)phenylacetamidomethyl resin using a double coupling program to yield linear protected compound attached to the resin, which is deprotected and cleaved from resin using hydrogen fluoride, dimethyl sulfide, anisole and p-thiocresol. Thereafter obtained linear Linaclotide is oxidized using dimethyl sulfoxide, and then the crude peptide was lyophilized and purified using Reverse phase-HPLC to obtain Linaclotide in 10-20% yield.

The above said patent has following drawbacks 1) the patent utilizes extremely toxic, corrosive and volatile hydrogen fluoride 2) oxidation using DMSO requires large volume of solvent, the oxidation time is too long. Therefore, throughout the production process, the oxidation step will occupy the large proportion.

*Biopolymers*, Issue 96, Volume 1, Pages 69-80 (2011) also discloses synthesis of Linaclotide by solid phase synthesis, following sequential addition of amino acids to the supported resin (Wang or 2-chlorotrityl resin) and thereafter cleaved from resin and deprotection is carried out in two steps. Oxidation of obtained peptide and followed by purification by RP-HPLC and lyophilization. This paper suggests the use of air, DMSO, red glutathione for oxidizing the linear Linaclotide peptide. Oxidation using air alone takes long duration (more than 24-48 hr) for completion and a high dilution is required.

The prior art as discussed above necessitates the isolation of crude Linaclotide by lyophilization before subjecting it into chromatographic purification. The said isolation is important to get the product in pure form, without any contamination. The principle disadvantage of lyophilization are 1) it requires high capital cost of equipment 2) it takes long process time and associated with high energy costs. Hence overall productivity is decreased.

WO 2012/118972 discloses a process for the preparation of Linaclotide by coupling the two fragments in solution phase in presence of a coupling agents HBTU, Cl-HOBt, DIPEA, DMF to obtain linear protected Linaclotide, which is deprotected in presence of TFA:EDT:TIS:$H_2O$ and oxidation in presence of sodium bicarbonate and glutathione hydrochloride, followed by purification using preparative RP-HPLC and lyophilization. Since the peptide synthesis is carried out in solution phase, the obtained product is often contaminated with undesired peptide as a byproduct and hence removal of this byproduct becomes tedious.

WO 2014/188011 discloses a process for the preparation of Linaclotide by solid phase synthesis. This publication utilizes DMSO as an oxidizing agent and the said reaction took more than 24 hour for completion thereby the productivity is decreased.

Considering the importance of Linaclotide as a medicinal product, there is a need to increase the productivity of the said peptide. The present inventors have made Linaclotide by the process, which is simple and industrially scalable with consistent yields. Further, the Linaclotide obtained by the process of the present invention results in higher yield and purity. Applicant surprisingly found that the Linaclotide can be manufactured in pure form by oxidizing the linear Linaclotide utilizing combination of air and oxidizing agent there by productivity is increased and the product formation is kinetically favored.

Applicant also find that purification of Linaclotide applying reversed phase high performance liquid chromatography (RP-HPLC) comprising a first, second and a third chromatography steps with a mixture of an aqueous buffer or aqueous acid with an organic solvent for elution yields high purity compound.

OBJECTIVE OF INVENTION

An objective of the present invention is to provide a process for preparing Linaclotide, which is simple, industrially applicable and robust.

Another objective of the present invention is to provide a process for preparing Linaclotide, which yields high purity product.

Still another objective of the present invention is to provide a process for preparing Linaclotide, which result in high yield.

Yet another objective of the present invention is to reduce the production cycle time thereby increasing the productivity.

SUMMARY OF THE INVENTION

The present invention relates to a process for the preparation of Linaclotide of formula (I),

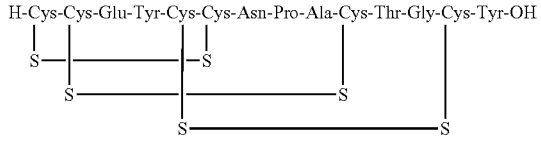

Formula (I) SEQ ID NO: 1 which comprises the following steps:
   a) obtaining the protected compound of formula (II),
      Y-Cys(Z)-Cys(Z)-Glu(X)-Tyr(X)-Cys(Z)-Cys(Z)-Asn(Y)-Pro-Ala-Cys(Z)-Thr(X)-Gly-Cys(Z)-Tyr(X)-⊛ Formula (II) SEQ ID NO: 1
   b) cleavage of the resin from the compound of formula (II) followed by deprotection of the protecting groups to obtain a compound of formula (III);
      $H_2N$-Cys(SH)-Cys(SH)-Glu-Tyr-Cys(SH)-Cys(SH)-Asn-Pro-Ala-Cys(SH)-Thr-Gly-Cys(SH)-Tyr-OH Formula (III) SEQ ID NO: 1
   c) oxidizing the compound of formula (III) utilizing a combination of air and oxidizing agent to obtain Linaclotide of formula (I); and
   d) purifying the crude utilizing RP-HPLC.
wherein Z represents a thiol protecting group; X represents a carboxyl, a phenol and an alcohol protecting group; Y represents an amino protecting group and ⊛ represents a resin.

Another aspect of the present invention relates to a process for the preparation of Linaclotide of formula (I),

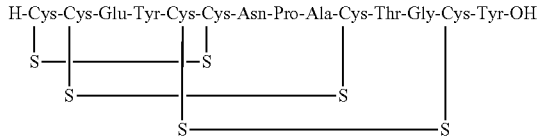

Formula (I) SEQ ID NO: 1 which comprises the following steps:
   a) obtaining the compound of formula (III),
      $H_2N$-Cys(SH)-Cys(SH)-Glu-Tyr-Cys(SH)-Cys(SH)-Asn-Pro-Ala-Cys(SH)-Thr-Gly-Cys(SH)-Tyr-OH Formula (III) SEQ ID NO: 1
   b) oxidizing the compound of formula (III) utilizing a combination of air and $H_2O_2$ to obtain Linaclotide of formula (I); and
   c) purifying the crude utilizing RP-HPLC.

Another aspect of the present invention relates to a process for the purification of Linaclotide applying reversed phase high performance liquid chromatography (RP-HPLC) comprising a first, second and a third chromatography steps with a mixture of an aqueous buffer or aqueous acid with an organic solvent for elution.

BRIEF DESCRIPTION OF ABBREVIATIONS

HBTU—O-Benzotriazole-N,N,N',N'-tetramethyluroniumhexafluorophosphate
Cl-HOBt—6-chlorol-hydroxy-benzotriazole
HOBt—Hydroxy benzotriazole
TBTU—O-(benzotriazol-1-yl)-N,N,N',N'-tetramethyluronium tetrafluoroborate,
DCC—1,3-dicyclohexylcarbodiimide
DIC—Diisopropylcarbodiimide
HBTU—O-(benzotriazol-1-yl)-1,1,3,3-tetramethyluroniumhexafluorophosphate
BOP—Benzotriazol-1-yl-oxy-tris(dimethylamino)phosphonium hexafluorophosphate
PyBOP—Benzotriazol-1-yloxytri(pyrrolidino)phosphonium hexafluorophosphate
PyBrOP—Bromotri(pyrrolidino)phosphonium hexafluorophosphate
PyClOP—Chlorotri(pyrrolidino)phosphonium hexafluorophosphate (PyClOP),
Oxyma—Ethyl-2-cyano-2-(hydroxyimino)acetate (Oxyma Pure),
TCTU—O-(6-Chlorobenzotriazol-1-yl)-1,1,3,3-tetramethyluronium tetrafluoroborate
EEDQ—Ethyl 1,2-dihydro-2-ethoxyquinoline-1-carboxylate
COMU—1-Cyano-2-ethoxy-2-oxoethylidenaminooxy)dimethylamino morpholinocarbenium hexafluorophosphate
DIPEA—N,N-diisopropylethylamine
DMF—N,N-dimethylformamide
DCM—Dichloromethane
THF—Tetrahydrofuran
NMP—N-Methyl pyrrolidine
DMAC—Dimethylacetamide
TFA—Trifluoro acetic acid
EDT—Ethanedithiol
TIS—Triisopropyl silane
DTT—Diothreitol
DMS—Dimethyl sulfide
DMSO—Dimethyl sulfoxide
MTBE—Methyltert-butylether
MeOH—Methanol
IPA—Isopropyl alcohol
CTC—Chlorotrityl chloride
Trt—Trityl
Acm—Acetamidomethyl
StBu—S-tert-butylmercapto
Tmob—Trimethoxybenzyl
DMT—dimethoxy trityl
MMT—Methoxytrityl
Fmoc—9-fluorenylmethoxycarbonyl Boc—tert-butoxycarbonyl
Cbz—Benzyloxycarbonyl
Bpoc—2-(4-biphenyl)-2-propyloxycarbonyl
TACM—S-Trimethylacetamidomethyl
DEPBT—3-(Diethoxy-phosphoryloxy)-3H-benzo[d][1,2,3]triazin-4-one

DETAILED DESCRIPTION OF THE INVENTION

In an embodiment, the present invention relates to an improved process for the preparation of Linaclotide. Accordingly the Linaclotide can be prepared either by solid phase synthesis or by solution phase synthesis or by sequential addition of peptide or by fragment based coupling, preferably by solid phase synthesis using sequential addition of peptide.

The process of solid phase synthesis of peptides comprises coupling of Nu-amino protected amino acid with a peptide resin, the Nu-amino protecting group is cleaved off and the resulting free amino group is coupled via peptide linkage to the carboxyl group of a second Nu-amino protected amino acid and the cycle repeated until the compound of formula (II) has been obtained and then said peptide is cleaved from said resin followed by deprotection of amino acid yields to compound of formula (III). Optionally, a washing step with a washing solution is performed after each deprotecting and coupling step. Oxidation of obtained compound of formula (III) followed by purification and lyophilization yields pure Linaclotide.

In yet another embodiment of the present invention, the Nu-amino protecting groups are selected from but not limited to a group comprising Fmoc, Boc, Cbz, Bpoc, and the like. Preferably Fmoc protected solid phase peptide synthesis is used.

In yet another embodiment of the present invention, the solid phase synthesis is carried out on an insoluble polymer which is acid sensitive. An acid sensitive resin is selected from a group comprising chlorotrityl resin (CTC), Sasrin, Wang Resin, 4-methytrityl chloride, TentaGel S, TentaGel TGA, Rink acid resin, NovaSyn TGT resin, HMPB-AM resin, 4-(2-(amino methyl)-5-methoxy)phenoxy butyric acid anchored to polymeric resin MBHA, 4-(4-(amino methyl)-3-methoxy)phenoxy butyric acid anchored to polymeric resin MBHA and 4-(2-(amino methyl)-3,3-dimethoxy)phenoxy butyric acid anchored to polymeric resin MBHA include, most preferred super acid labile resin is 2-chlorotrityl resins.

In still another embodiment of the present invention, the coupling reagent used in the above process of sequential coupling of amino acid comprises o-(7-azabenzotriazol-1-yl)-1,1,3,3-tetramethyluronium hexafluorophosphate (HATU), o-(benzotriazol-1-0)-1,1,3,3-tetramethyluroniumhexafluorophosphate (HBTU), o-(benzotriazol-1-yl)-1,1,3,3-tetramethyluronium tetrafluoroborate (TBTU), benzotriazole-1-yl-oxy-tris(dimethylamino)phosphonium hexafluorophosphate (BOP), benzotriazole-1-yl-oxy-tris-pyrrolidinophosphonium hexafluorophosphate (PyBOP), N,N-bis-(2-oxo-3-oxazolidinyl)phosphonic dichloride (BOP-Cl), bromo-tris-pyrrolidino-phosphonium hexafluorophosphate (PyBroP), iso-butylchloroformate (IBCF), 1,3 dicyclohexylcarbodiimide (DCC), 1,3-diisopropyl-carbodiimide (DIC), 1-(dimethylaminopropyl)-3-ethylcarbodiimide hydrochloride (WSCDI), N-ethoxycarbonyl-2-ethoxy-1,2-dihydroquinoline (EEDQ), isopropylchloroformate (IPCF), 2-(5-norbornen-2,3-dicarboximido)-1,1,3,3-tetramethyluronium tetrafluoroborate (TNTU), propane phosphonic acid anhydride (PPAA), 2-succinimido-1,1,3,3-tetramethyluronium tetrafluoro borate (TSTU), PyClOP, Oxyma pure, TCTU, COMU, HOBt or DEPBT In still another embodiment of the present invention, the coupling reaction is carried out in presence of a base and in the presence of solvent. The base is organic or inorganic base. The inorganic base comprises potassium carbonate, lithium carbonate, sodium carbonate, sodium ethoxide, sodium bicarbonate, potassium bicarbonate, sodium hydroxide, potassium hydroxide, ammonium hydroxide, and mixtures thereof; the organic base comprises diisopropylamine, N,N-diisopropylethylamine triethylamine, dimethylamine, trimethyl amine, isopropyl ethylamine, pyridine, N-methyl morpholine, piperidine, N,N-dimethylaminopyridine, 1,8-diazabicyclo[5.4.0]undec-7-ene (DBU), and/or mixtures thereof. The solvent comprises dimethylformamide (DMF), dimethylsulfoxide (DMSO), N-Methyl pyrrolidine (NMP), Dimethylacetamide (DMAC), dichloromethane (DCM), methanol, isopropanol, dichloroethane, 1,4-dioxane, tetrahydrofuran (THF), 2-methyl tetrahydrofuran ethyl acetate, acetonitrile, acetone, and the like or mixtures thereof.

In yet another embodiment of the present invention, the side chain in an amino acid is, optionally, protected using a protecting groups for the amino group include, but are not limited to, acetyl (Ac), Boc, Cbz, 2-chlorobenzyloxycarboyl (2-Cl-Cbz), 2-bromobenzyloxycarbonyl (2-BrCbz), 4-methlytrityl (Mtt), benzyloxycarbonyl (Z), Fmoc, 1-(4,4-dimethyl-2,6-dioxocyclohex-1-ylidene)ethyl (Dde), and trifluoroacetyl (Tfa), preferably Fmoc. The removal of protecting group is carried out by conventional methods, for example the removal of Fmoc protection is carried out using a secondary amine base comprises piperidine, dimethylamine, diethylamine, diphenylamine or mixtures thereof. The suitable side chain protecting groups for a hydroxyl group include, but are not limited to, benzyl (Bzl), tert-butyl (tBu), and trityl (Trt). The suitable side chain protecting groups for a thiol group include, but are not limited to, acetamidomethyl (Acm), Bzl, tBu, tert-butylthio (tButhio), p-methoxybenzyl (pMeoBzl), and 4-methoxytrityl (Mmt). The suitable side chain protecting groups for a phenolic hydroxyl group include, but are not limited to, tetrahydropyranyl, tBu, Trt, Bzl, Cbz, z-Br-Cbz, and 2,5-dichlorobenzyl. The suitable side chain protecting groups for a carboxylic acid include, but are not limited to benzyl, 2,6-dichlorobenzyl, tBu, and cyclohexyl.

In one more embodiment of the present invention cleavage of the resin from compound of formula (II), and deprotection can be carried out either in a single step or two step processes.

In still another embodiment of the present invention, wherein the peptide is cleaved from the resin using a mild reagent comprising about 0.1% to about 5% of TFA in an organic inert solvent or a mixture of acetic acid with trifluoroethanol and DCM. After reaction the reaction mass is neutralized with a base comprises piperidine, dimethylamine, diethylamine, diphenylamine, sodium bicarbonate, potassium bicarbonate, sodium carbonate, sodium hydroxide and the like, preferably 1-15% of organic base is used.

In other embodiment of the present invention, wherein the organic inert solvent is selected from the group comprising of DCM, chloroform, dichloro ethanol, ethyl acetate and the like or mixtures thereof.

In still another embodiment of the present invention, removal of protecting groups of the peptide may be affected by addition of a strong acidic composition. The acidic composition is preferably based on an acidic material such as TFA, and contains scavenger reagents including, but not limited to, ethanedithiol (EDT), Diothreitol (DTT), TIS (triisopropylsilane), ammonium iodide, 2,2'-(ethylenedioxy) diethane, acetyl cystein, DMS, phenol, cresol and thiocresol or mixture thereof and water. The relative ratio of acidic material to scavenger to water may be from about 85% to about 99% acidic material, from about 0.1% to about 15% scavenger, and from about 0.1% to about 15% water by weight.

In other embodiment of the present invention, the oxidizing agent is selected from a group comprising of hydrogen peroxide, dimethyl sulfoxide (DMSO), glutathione, iodine and the like and a mixture thereof. Preferably the oxidation step comprises the use of air and $H_2O_2$ in presence of buffer. Applicant surprisingly found that the use of combination of air and $H_2O_2$ for oxidation proceeds smoothly and resulted with desired intra molecular disulphide bridges and provides the product in good purity, whereas the prior art process are often associated with intermolecular disulphide bond leading to the formation of multimer and undesired products. Further because of the use of combination of air and $H_2O_2$ the oxidation completes within 1-6 hours, preferably 1-3 hours and yields desired product without contamination of multimer type impurities thereby overall productivity is increased. Applicant found addition of oxidizing agent in portion wise helps to get desired product in shorter time in commercial scales.

In yet another embodiment of the present invention, the buffer used during the oxidation steps is selected from a group comprising ammonium acetate, sodium carbonate, ammonium bicarbonate, water, and the like, and a mixture thereof. The oxidation is carried out in a buffer solution at a pH range of about 7 to about 9.

In another embodiment of the present invention, purification of Linaclotide applying reversed phase high performance liquid chromatography (RP-HPLC) comprising a first, second and a third chromatography steps with a mixture of an aqueous buffer or aqueous acid with an organic solvent for elution.

In another embodiment of the present invention, purification of Linaclotide is carried out by successive Reverse Phase HPLC. The RP-HPLC is expediently performed using a commercially available silica gel sorbent as stationary phase. The elution is carried out either by isocratic condition or by gradient mode. Common mobile phases used for elution include, but not limited to, aqueous buffer comprises ammonium acetate buffer, or water containing acid such as acetic acid (0.001% to 5%), formic acid (0.001% to 5%), TFA (0.001% to 5%), and the like, or any miscible combination of water with various organic solvents like THF, acetonitrile and methanol. The purification system preferably employs gradient elution; preferably gradient elution is performed by either increasing or decreasing the amounts of an organic modifier. Suitable organic modifiers include, but are not limited to, acetonitrile, THF, ethanol, methanol, ethanol, n-propanol or iso-propanol. Ultraviolet (UV) absorption of wavelength in the range of 200 nm to 320 nm was used to monitor.

In other embodiment of the present invention, the first chromatography step is preferably carried out using ammonium acetate and acetonitrile, second chromatography step using TFA/water; acetonitrile and the third chromatography step using acetic acid/water; acetonitrile.

In still another embodiment of the present invention, all synthetic steps of the above described process are performed under mild conditions providing products containing a low content of by-products and producing a final product in high yield and high purity.

In one more embodiment of the present invention, the Linaclotide is preferably prepared by following the sequential addition of amino acid as shown below:

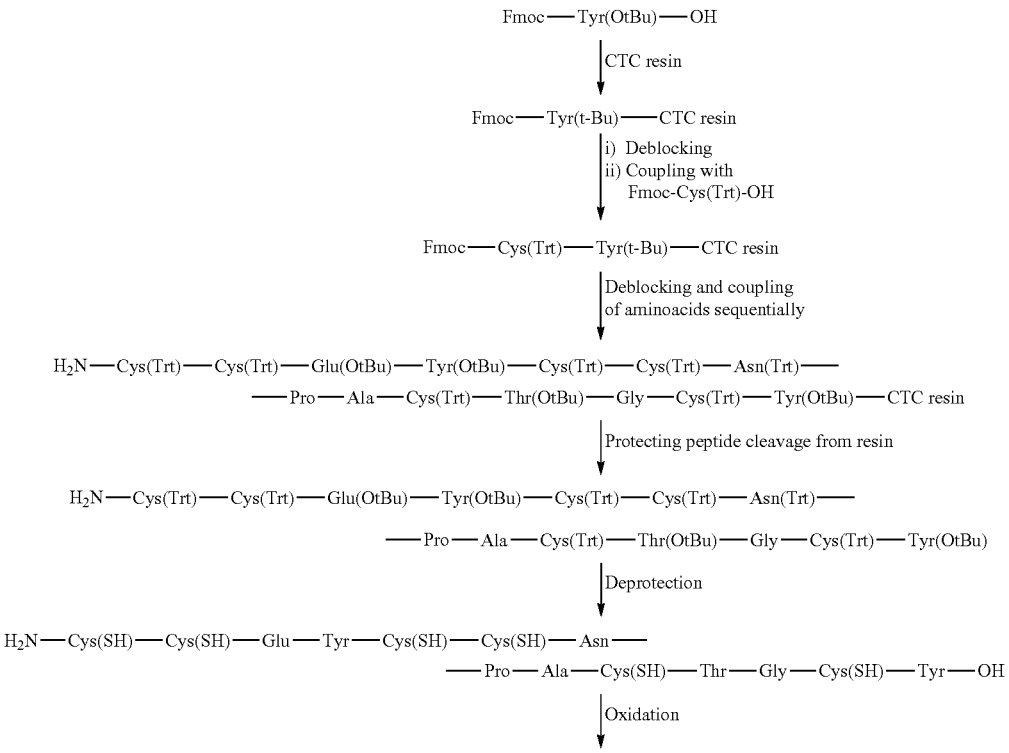

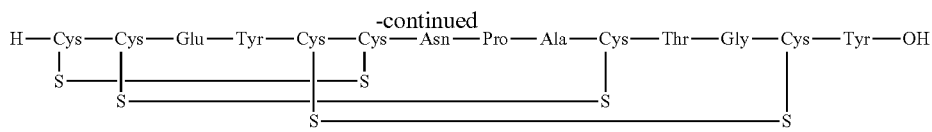

SEQ ID NO: 1

The invention is illustrated with the following examples, which are provided by way of illustration only and should not be construed to limit the scope of the invention in any manner whatsoever.

Example-1

Process for Preparing Linear Protected Linaclotide (II)

2-ChloroTrityl Resin (CTC Resin) (65 g) (1.6 mmol/g) was transferred to a glass reaction vessel containing a sintered disk. Anhydrous dichloromethane (400 ml) was added to the glass vessel and drained after two min. A clear solution of Fmoc-Tyr(OtBu)-OH (29 g, 1.1 eqv.) dissolved in dry DCM (300 ml) and N,N di-isopropylethylamine (41 ml) was added. The reaction mixture was stirred mechanically for 3 hrs and the solution was drained out, and the resin was washed with 1% DIPEA in DCM (400 ml). The peptide resin was washed with a mixture of 1:1 [10% DIPEA: Methanol; 300 ml], 1% DIPEA in DCM (400 ml), 0.5% DIPEA in MTBE (300 ml) and dried under vacuum.

Step (2): Coupling of Fmoc-Cys (Trt) to Tyr (OtBu)-CTC-Resin

Fmoc-Tyr(OtBu)-Resin from step (1), was swelled in dichloromethane (250 ml) for 20 min and dimethylformamide (DMF) (250 ml) for 20 min. 20% piperidine in DMF (300 ml) (5+15 min) was added to the Fmoc-Tyr (OtBu)-Resin and the resin was washed with DMF (300 ml), Isopropylalcohol (IPA) (200 ml) and DMF (300 ml). Thereafter resin beads were taken out and checked for Kaiser Test (positive) and chloranil test (positive). To this resin a solution consisting of Fmoc-Cys(Trt)-OH (68 g; 2 eqv); HOBT (16 g; 2 eqv) dissolved in DMF (300 ml) and DIC (27 ml; 3 eqv) was added and the reaction was allowed at 25° C. for 2 hrs, followed by washing with DMF (300 ml) to obtain Fmoc-Cys(Trt)-Tyr(OtBu)-Resin.

Remaining aminoacids (Fmoc-Gly-OH; Fmoc-Thr (OtBu)-OH; Fmoc-Cys (Trt)-OH; Fmoc-Ala-OH; Fmoc-Pro-OH; Fmoc-Asn (Trt)-OH; Fmoc-Cys (Trt)-OH; Fmoc-Cys (Trt)-OH; Fmoc-Tyr (OtBu)-OH; Fmoc-Glu (OtBu)-OH; Fmoc-Cys (Trt)-OH and Fmoc-Cys (Trt)-OH) were sequentially coupled in similar manner to get desired linear Linaclotide (III)

Example-2

Process for Preparing Linear Linaclotide (III)

Step (1): Cleavage of Protected Linaclotide from the Peptide Resin

The experiment conducted for cleavage of Linaclotide (protected) from the peptide resin (190 g) was carried out by using 1% TFA in DCM (4×300 ml) and the resulting solution was neutralized by using 10% DIPEA in DCM (4×100 ml). The fractions which were found to be UV positive were collected, combined and evaporated. The crude was dissolved in ethyl acetate (1.5 L) and the organic layer was washed with water (250 ml); and 0.1M NaCl Solution (250 ml). The organic layer was dried over sodium sulphate, filtered and evaporated to a solid. The solid was treated with MTBE, filtered and dried under vacuum for 16 hrs.

Weight: 145 g

Step (2): Deprotection of Protected Linaclotide 50 g of protected peptide obtained above was added to the reactor containing cold solution (500 ml) of 80% TFA (400 ml), 5% TIS (25 ml), 10% $H_2O$ (50 ml), 5% EDT (25 ml); stirred the cocktail for 30 min at 0-5° C. and filtered the solid and the TFA cocktail was stirred for 2 hours at room temperature. After two hours the solution was filtered and precipitated by the addition of 10 volumes of MTBE (5 L). The obtained product was filtered and washed with MTBE and dried under vacuum to obtain linear crude product.

Yield: 24 g

HPLC Purity: 81%.

Example-3

Process for Preparing Linear Linaclotide (III)

The experiment conducted for cleavage of Linaclotide (protected) from the peptide resin (190 g) was carried out by using 1% TFA in DCM (4×300 ml) and the resulting solution was neutralized by using 10% DIPEA in DCM (4×100 ml). The fractions which were found to be UV positive were collected, combined and evaporated to get residue containing trace amount of DCM. To residue, was added to the reactor containing cold solution (1500 ml) of 80% TFA (1200 ml), 5% TIS (75 ml), 10% $H_2O$ (150 ml), 5% DTT (75 gm); stirred the cocktail for 30 min at 0-5° C. and filtered the solid and the TFA cocktail was stirred for 2 hours at room temperature. After two hours the solution was filtered and precipitated by the addition of 10 volumes of MTBE (15 L). The obtained product was filtered and washed with MTBE and dried under vacuum to obtain linear crude product.

Yield: 70 g; HPLC Purity: 80%.

Example-4

Process for Preparing Linaclotide (I)

Linear Linaclotide (10 g) was dissolved in degassed ammonium bicarbonate (10 L). After dissolution of the compound, compressed air was slowly bubbled and added the hydrogen peroxide (qty: 0.4 ml) in portion wise and stirred for 1 hour. After completion of the reaction (monitored by reverse phase analytical HPLC) the oxidized product was purified by reverse phase HPLC without isolation.

Oxidized Product Purity: 70%

| Oxidizing Agent | Remarks |
| --- | --- |
| Air | Reaction takes about 24-48 Hr |
| hydrogen peroxide | Reaction takes 5-10 minutes and results with degraded product (multimer formation; kinetically controlled), due to wrong folding |
| Combination of air and hydrogen peroxide | Reaction takes about 1-3 Hr and results with desired Linaclotide (thermodynamically controlled) |

From the table it is evident that the combination of air an hydrogen peroxide helps to achieve the desired product in reduced reaction cycle time and thereby the overall productivity is increased.

Example-5

Purification of Crude Linaclotide

Stage-1

The oxidized crude peptide solution obtained from the example 4 was passed through RP-HPLC column (C18 reverse phase column, mobile phase: A: 0.01 M ammonium acetate mobile phase B: acetonitrile) and eluted.

Stage-2

The main pool obtained from the stage-1 was re-purified on reverse phase HPLC (C18 reverse phase column, mobile phase: A: 0.1% TFA in water/ACN; mobile phase B: acetonitrile). Fractions were analyzed using SEC. The fractions having the purity greater than 98% were taken and pooled and taken to the next stage purification.

Stage-3

The main pool obtained from the stage-2 were diluted with equal amount of water and passed through RP-HPLC (C18 reverse phase column, mobile phase: A: 0.1% acetic acid in water/ACN; mobile phase B: acetonitrile) and eluted. The fractions were checked on analytical HPLC for purity. The pure fractions (>98%) were pooled and lyophilized to obtain Linaclotide.

Yield: 1.5 g

HPLC purity: 98.9%

Example-6

Purification of Crude Linaclotide

Stage-1

The oxidized crude peptide solution obtained from the example (4) was passed through RP-HPLC column (C18 reverse phase column, mobile phase: A: 0.01 M ammonium acetate; mobile phase B: acetonitrile) and eluted.

Stage-2

The main pool obtained from the stage-1 was re-purified on reverse phase HPLC (C18 reverse phase column, mobile phase: A: 0.1% TFA in water/ACN; mobile phase B: acetonitrile). Fractions were analyzed using SEC. The fractions having the purity greater than 98% were taken and pooled and taken to the next stage purification.

Stage-3

The main pool obtained from the stage-2 were diluted with equal amount of water and passed through RP-HPLC (C18 reverse phase column, mobile phase: A: 0.1% acetic acid in water/ACN; mobile phase B: acetonitrile) and eluted. The fractions were checked on analytical HPLC for purity. The pure fractions (>98%) were pooled and lyophilized to obtain Linaclotide.

Yield: 2.0 g; HPLC purity: >99%

We claim:

1. A process for the preparation of Linaclotide of formula (I) having purity greater than 99% by HPLC Formula (I) SEQ ID NO: 1

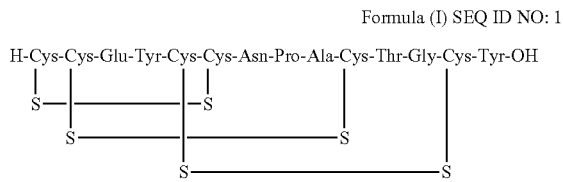

which consists the steps of:
a) obtaining the compound of formula (III), by sequential addition of amino acids H$_2$N-Cys(SH)-Cys(SH)-Glu-Tyr-Cys(SH)-Cys(SH)-Asn-Pro-Ala-Cys(SH)-Thr-Gly-Cys(SH)-Tyr-OH Formula (III) SEQ ID NO: 1 b) oxidizing the compound of formula (III) utilizing a combination of air and hydrogen peroxide to obtain Linaclotide of formula (I); and c) purifying the obtained Linaclotide in step (b) utilizing RP-HPLC in a three stage purification.

2. The process as claimed in claim 1, wherein obtaining the compound of formula (III) is by cleaving the resin from the peptide of formula (II)

Y-Cys(Z)-Cys(Z)-Glu(X)-Tyr(X)-Cys(Z)-Cys(Z)-Asn(Y)-Pro-Ala-Cys(Z)-Thr(X)-Gly-Cys(Z)-Tyr(X)-⬤ Formula (II) SEQ ID NO: 1 and deprotecting the protecting groups; wherein Z represents a thiol protecting group; X represents a carboxyl, a phenolic or an alcohol protecting groups; Y represents an amino protecting group and ⬤ represents a resin.

3. The process as claimed in claim 1, wherein the oxidizing step is accomplished in the presence of a buffer solution.

4. The process as claimed in claim 3, wherein the buffer solution is selected from an aqueous solution of ammonium acetate, sodium carbonate, ammonium bicarbonate or mixtures thereof.

5. The process as claimed in claim 1, wherein the oxidizing step is at a pH in the range of 7 to about 9.

\* \* \* \* \*